United States Patent
Ein-Gal

(10) Patent No.: US 9,555,267 B2
(45) Date of Patent: Jan. 31, 2017

(54) DIRECT CONTACT SHOCKWAVE TRANSDUCER

(71) Applicant: Moshe Ein-Gal, Ramat Hasharon (IL)

(72) Inventor: Moshe Ein-Gal, Ramat Hasharon (IL)

(*) Notice: Subject to any disclaimer, the term of this patent is extended or adjusted under 35 U.S.C. 154(b) by 354 days.

(21) Appl. No.: 14/181,747

(22) Filed: Feb. 17, 2014

(65) Prior Publication Data
US 2015/0231414 A1 Aug. 20, 2015

(51) Int. Cl.
*A61N 7/00* (2006.01)

(52) U.S. Cl.
CPC ........................ *A61N 7/00* (2013.01)

(58) Field of Classification Search
CPC ............ A61B 17/2256; A61B 17/22004; A61B 17/2202; A61B 17/2251; A61N 7/022; A61N 2007/0078
See application file for complete search history.

(56) References Cited

U.S. PATENT DOCUMENTS

| 4,669,472 A | 6/1987 | Eisenmenger |
| 5,131,392 A | 7/1992 | Jolesz |
| 6,217,530 B1 | 4/2001 | Martin |
| 2008/0161692 A1 | 7/2008 | Podmore |

FOREIGN PATENT DOCUMENTS

| DE | 202007007920 | 10/2008 |
| DE | 202010009899 | 10/2010 |
| EP | 2289435 | 3/2011 |

OTHER PUBLICATIONS

PCT Written Opinion PCT/IB2015/051155, May 18, 2015.

*Primary Examiner* — Joel Lamprecht
(74) *Attorney, Agent, or Firm* — Dekel Patent Ltd.; David Klein

(57) ABSTRACT

A system is attachable to a surface of a tissue of a patient for applying pressure pulses to the tissue. The system includes a shockwave transducer that has a shockwave generating portion and a solid transducer interface arranged to directly contact a tissue of a patient. The shockwave generating portion includes an electrical-to-shockwave energy converter operable to generate shockwaves. The transducer interface includes an electrically safe and bio-compatible material arranged to transmit the shockwaves from the shockwave generating portion to the tissue.

13 Claims, 1 Drawing Sheet

DIRECT CONTACT SHOCKWAVE TRANSDUCER

FIELD OF THE INVENTION

The present invention relates to a method and a system for shockwave generation and shockwave treatment, wherein the shockwave generator (transducer) is in direct contact with a part of the patient's body without using a propagating liquid.

BACKGROUND OF THE INVENTION

Electromagnetic shockwave systems for medical purposes, such as lithotripsy, treating pathological tissue conditions and many others, are well known. For example, U.S. Pat. No. 5,233,972 to Rattner describes an electromagnetic or electrodynamic shockwave system in which the shockwaves are generated by a movable element driven by electromagnetic interaction with a stationary element. The shockwave source has a coil arrangement which serves as the stationary element, and which is attached to an insulator member in the shockwave source. A membrane of electrically conductive material is employed as the movable element, and is disposed opposite the stationary coil arrangement. When the coil arrangement is charged with a high-voltage pulse, currents are induced in the membrane in a direction opposite to the direction of the current flowing in the coil arrangement. As a consequence of the opposite magnetic fields arising due to the respective flows of current in the coil arrangement and in the membrane, the membrane is subjected to repelling forces which suddenly and rapidly move the membrane away from the coil.

Ratner describes the transformation of a pressure wave to a shockwave: "A pressure pulse is thereby introduced into an acoustic propagation medium disposed adjacent the membrane. This pressure pulse intensifies during its path through the propagation medium to form a shockwave, as a consequence of the non-linear compression properties of the propagation medium".

The non-linear effect increases with increased peak pressure. Shockwave formation, therefore, takes place over a formation distance inversely proportional to the wave's peak pressure. The formation distance is shortened by focusing the wave and increasing the peak pressure. Kidney stones disintegration, for example, is commonly carried out by focused waves where shockwave formation starts in water and is completed in (water-equivalent) tissue. A typical shockwave formation distance (from repelling membrane to focal zone) is in the range of 10-30 cm.

Referring to the term "shockwave", Rattner states: "For simplicity, the waves in the propagation medium will always be referred to herein as shockwaves, and this term will encompass incipient shockwaves in the form of pressure pulses."

Another example of a prior art electromagnetic shockwave transducer (generator) is found in U.S. Pat. No. 5,230,328 to Buchholtz, et al. Pressure pulses are generated by "driving a membrane with a spiral coil arrangement having terminals connected to a high-voltage pulse generator which charges the coil with high-voltage pulses having an amplitude in the kilovolt range, for example, 20 kV. Such high-voltages can be generated, for example, by capacitor discharges. When the spiral coil arrangement is charged with such a high-voltage pulse, it generates a magnetic field extremely quickly. Simultaneously, a current is induced in the membrane, or at least in the electrically conductive region thereof, which is directed oppositely to the current flowing in the coil. The membrane current consequently produces an opposing magnetic field, causing the membrane to be rapidly moved away from the spiral coil arrangement. The pressure pulse initiated in the acoustic propagation medium, which is preferably a liquid such as water, is introduced in a suitable manner into the subject to be charged with the pressure pulses. As necessary, focusing of the pressure pulses may be undertaken before the pressure pulses reach the subject, for example by means of an acoustic lens."

U.S. Pat. No. 5,374,236 to Hassler also describes an electromagnetic coil system for generating pressure pulses which are applied to the body surface of the patient by means of a flexible coupling pillow, filled with a liquid medium for acoustic coupling. "As a consequence of the flexibility of the coupling pillow, the spacing of the pressure pulse source from the body surface can be set, while maintaining contact between the coupling pillow and the body surface, so that the focus of the pressure pulses lies in the zone to be treated."

Shockwaves are also produced and focused by a self-focusing array of piezoelectric elements. Examples include U.S. Pat. No. 4,721,106 to Kurtze et al. and U.S. Pat. No. 5,111,805 to Jaggy et al. Here again the waves propagate through a liquid acoustic propagation medium before reaching the patient.

Focusing shockwaves by a phased array of electromagnetic transducers is described in U.S. Pat. No. 5,131,392 to Jolesz et al. and US patent application 20090275832 to Gelbart et al. Here again the waves propagate through a liquid acoustic propagation medium before reaching the patient.

Thus, prior art electromagnetic and piezoelectric shockwaves transducers are configured to produce pressure waves in a propagation medium, typically water. Sufficient propagation distance enables focusing and shockwaves formation. The transducers and the focusing means are generally circularly symmetric and are configured to produce generally spherical converging waves.

SUMMARY OF THE INVENTION

The present invention seeks to provide a novel pressure waves treatment system and method, as is described more in detail hereinbelow, which has use in many medical applications, such as but not limited to, lithotripsy, orthopedics, treating pathological tissue conditions and many others, in particular, applications to soft tissue. Rattner's nomenclature relative to the term "shockwaves" is adopted and the term "shockwaves" may be used here interchangeably for pulses of pressure wave, including waves with long rise time.

In one non-limiting embodiment of the invention, a device and method are provided for producing, shaping and coupling pulses of pressure waves to a patient by direct contact of at least one transducer to a part of the patient's body, thus avoiding the usage of propagating liquid. Instead, the transducer incorporates a solid interface as the propagating medium. Coupling the transducer to the patient at such a close proximity is implemented with electrically safe and bio-compatible contact as well as with mechanically efficient matching of respective acoustic impedances of the patient and the transducer. Waves emanating from a single transducer are not necessarily focused. Focusing is obtainable by various methods, such as cupping the membrane, by shaping the solid interface as a lens or by configuring multiple transducers as a phased array where the transducers are respectively energized according to a timed sequence so as to assure simultaneous arrival of the waves from the respective transducers at a desired focal region.

In one embodiment, the transducer is an electromagnetic one. The transducer membrane is configured to be conformably attached to a part of a patient's body. Interaction of magnetic field and pulses of electrical current in the membrane cause the membrane to repel and transmit pressure waves into the patient.

According to another embodiment, the membrane is shaped according to application and curved so as to provide diverging, parallel or converging waves.

Another embodiment describes a multiplicity of electromagnetic or piezoelectric transducers attached to a patient's body as a phased array. Electromagnetic transducers may include membranes and piezoelectric transducers may include piezoelectric crystals. Each transducer is energized separately by current or voltage pulses, respectively.

Another embodiment describes the multiple transducers to be configured as concentric rings. Such a ring may be continuous or made of discrete transducers. The transducers may be electromagnetic or piezoelectric, for example. The face of the rings facing the patient may be planar or conical. Focusing is obtainable by individually energizing (triggering) the transducers according to respective distances of the transducers from the treated region, so as to provide simultaneous arrival of the waves at a focal region.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
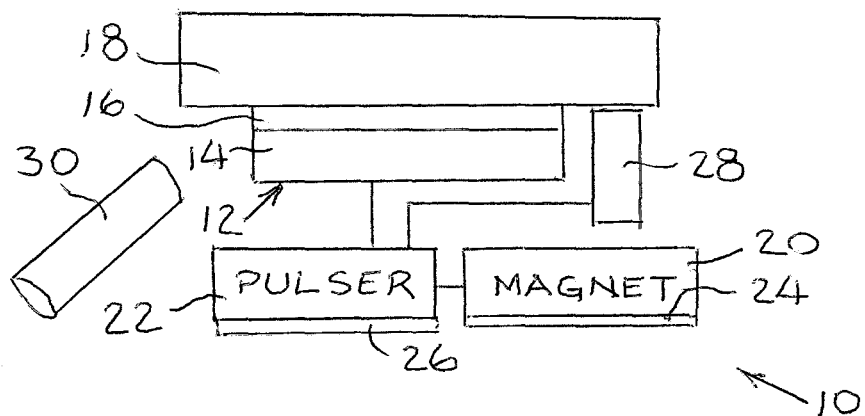
FIG. 1 is a simplified sectional illustration of a system for pressure wave generation or treatment, constructed and operative in accordance with an embodiment of the invention.

Reference is now made to FIG. 1, which illustrates a system 10 for shockwave generation or treatment, constructed and operative in accordance with a non-limiting embodiment of the invention.

System 10 includes a shockwave transducer 12 that includes a shockwave generating portion 14 and a solid (non-fluid) transducer interface (coupling interface) 16 arranged to contact a tissue 18 of a patient. The shockwave generating portion 14 of shockwave transducer 12 may include, without limitation, an electrical-to-shockwave energy converter (e.g., electro-hydraulic, electromagnetic or piezoelectric) that generates shockwaves (acoustic pressure pulses). The transducer interface 16 is preferably made of an electrically safe and bio-compatible material that exhibits mechanically efficient matching of respective acoustic impedances of the patient and the transducer. Preferably, the coupling interface 16 has an acoustic impedance not lower than that of tissue 18 and not higher than that of shockwave generating portion 14, most preferably close (within 20%) to the geometric mean of the two.

The acoustic impedance (Z) of a material is defined as the product of its density (ρ) and acoustic velocity (V), that is, $Z=\rho*V$.

The acoustic impedance (Z) is measured in Rayls (kg/(sec·m$^2$)] or more conveniently in MegaRayls (MRayls). The Z of typical biological materials is as follows (taken from "Basics of Biomedical Ultrasound for Engineers", Published Online: 9 Apr. 2010 and found at http://onlinelibrary.wiley.com/doi/10.1002/9780470561478.app1/pdf) as measured in MRayls:

Water 1.48
Blood 1.66
Fat 1.38
Liver 1.69
Kidney 1.65
Brain 1.60
Heart 1.64
Muscle (along the fibers) 1.68
Muscle (across the fibers) 1.69
Skin 1.99
Eye (lens) 1.72
Eye (vitreous humor) 1.54
Bone axial (longitudinal waves) 7.75
Bone axial (shear waves) 5.32
Teeth (dentine) 7.92
Teeth (enamel) 15.95

Some aluminum alloys have a Z of 17; copper alloys about 44 (these values are taken from http://www.ondacorp.com/images/Solids.pdf). Possible materials for coupling interface 16 include, without limitation, types of glass (Z in the range of 10-14 MRayls), types of ECCOSORB (available from Emerson & Cuming; Z in the range of 5-12 MRayls), titanium (Z about 27), plastics and boron carbide (Z about 26).

The coupling interface may incorporate multiple cascaded layers, each incorporating a respective acoustic impedance so as to provide adequate waves propagation in the coupling interface. The layer contacting the patient incorporates acoustic impedance close to that of the patient, so as to minimize waves' reflection at the interface with the patient and the associated damage to the skin of the patient.

In one non-limiting embodiment of the invention, shockwave generating portion 14 is a membrane made of an electrically conducting material (e.g., copper or aluminum alloy) or a membrane including an electrically conducting coil. The transducer interface 16 is a thin layer of a coupling interface attached to the outer surface of the membrane. The surface of the transducer 12 is attachable to the surface of tissue 18 such that the distance of the membrane 14 from the surface of the tissue 18 does not exceed a few millimeters (e.g., 2-20 mm).

The shockwave generating portion (membrane) 14 is configured to communicate with a magnet 20, which induces a magnetic field in the membrane 14, parallel to the outer surface of membrane 14. The shockwave generating portion (membrane) 14 is also configured to communicate with a pulser (electric pulse generator) 22. Pulser 22 delivers pulses of electrical current. The current orientation is parallel to the outer surface of shockwave generating portion (membrane) 14 and is generally not parallel to the magnetic field in membrane 14. Shockwave generating portion (membrane) 14 is configured to repel and deliver pressure pulses to the coupling interface 16 in response to the interaction between the magnetic field and the current pulses in the membrane 14.

The membrane 14 can be flat, but the invention is not limited to this shape, and in general, membrane 14 can be at least partially concave, planar or convex.

Magnet 20 may be an electromagnet that includes at least one electromagnet induction coil 24. In one embodiment, pulser 22 delivers current pulses to membrane 14 by induction from at least one pulser induction coil 26. In another embodiment, there is one or more common induction coils (24 or 26) and pulser 22 delivers the current pulses to membrane 14 by induction from the common induction coil(s). The induction coils (24 or 26 or common induction coil) may be coils in one or more layers of one or more printed circuit boards.

In one non-limiting embodiment of the invention, system 10 combines shockwave transducer 12 with one or more other transducers 28 for delivering energy, such as but not limited to, an optical energy, an ultrasonic energy, an RF energy, a magnetic energy, a microwave energy generator and/or mechanical energy generator (e.g., a spring or oscillating mass). The delivery of the additional energy is synchronized with the current pulses delivered by pulser 22 or controller (sequencer) 23 (FIG. 2) in communication with the transducers (the controller in the case of a piezoelectric transducer). An imager 30 may be provided for imaging the delivery of the shockwaves to the tissue.

Figure 2:
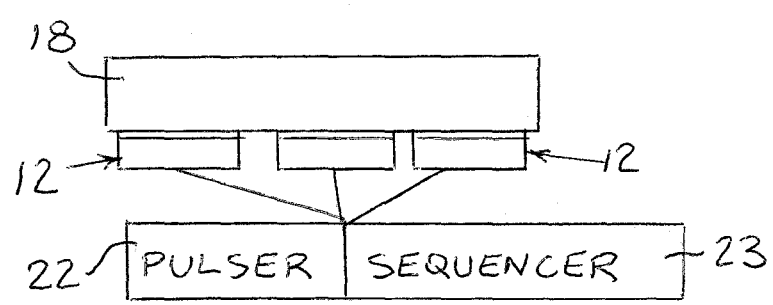
FIG. 2 is a simplified sectional illustration of a system for pressure wave generation or treatment, constructed and operative in accordance with another embodiment of the invention, and using a phased array of transducers.

Reference is now made to FIG. 2. In the embodiment of FIG. 1, the shockwaves emanating from the single transducer 12 are not necessarily focused. In the embodiment of FIG. 2, focusing is obtainable by multiple transducers 12 configured as a phased array. The transducers 12 are respectively energized according to a timed sequence so as to assure simultaneous arrival of the waves from the respective transducers at a desired focal region. In other words, pulser 12 delivers the electric current pulses to the shockwave transducers 12 in controlled trigger times.

Figure 3:
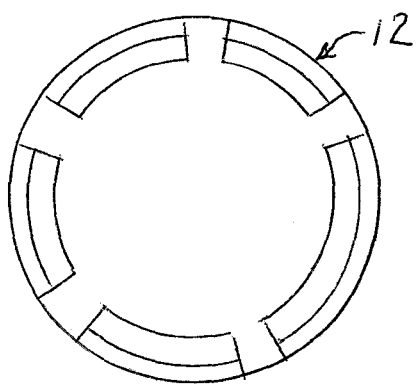
FIG. 3 is a simplified sectional illustration of a system for pressure wave generation or treatment, constructed and operative in accordance with another embodiment of the invention, and using a ring arrangement of transducers.

Reference is now made to FIG. 3. In this embodiment, multiple transducers 12 are arranged as concentric rings, either a continuous ring or made of discrete transducers. The transducers may be electromagnetic or piezoelectric, for example. The face of the rings facing the patient may be planar or conical.

Focusing for the phase array of FIG. 2 or 3 is obtainable by individually energizing (triggering) the transducers according to respective distances of the transducers from the treated region, so as to provide simultaneous arrival of the waves at a focal region.

The following parameters are defined:

$T_z$=the simultaneous arrival time of the respective waves at the focal region, $T_i$=the time of the energizing pulse associated with the $i^{th}$ transducer, $D_i$=the distance between the $i^{th}$ transducer and the focal region, and $C_i$=the average propagation speed of the wave associated with the $i^{th}$ transducer.

$T_i$ is then given by:

$$T_i = T_z - D_i/C_i.$$

The instantaneous propagation speed may vary during propagation according to the tissue through which a wave propagates. The distance $D_i$ and the associated tissue (for calculating the average propagation speed $C_i$) are determinable, for example, from 3D imaging of the patient or by acoustically measuring the distance between a transducer and the treated region.

FIG. 3 also illustrates that focusing can be obtained by cupping or curving the solid coupling interface or by shaping it as a lens (e.g., concave or convex).

What is claimed is:

1. A system attachable to a surface of a tissue of a patient for applying pressure pulses to the tissue, the system comprising:
    a shockwave transducer comprising a shockwave generating portion and a solid transducer interface arranged to directly contact a tissue of a patient, said shockwave generating portion comprising an electrical-to-shockwave energy converter operable to generate pulses of pressure waves, and said transducer interface comprising an electrically safe and bio-compatible material arranged to transmit said shockwaves from said shockwave generating portion to the tissue;
    a magnet operable to induce a magnetic field in said shockwave generating portion; and
    a pulser operable to deliver electrical current pulses to said shockwave generating portion, wherein said shockwave generating portion generates shockwaves in response to said magnetic field and said electric current pulses, and wherein the acoustic impedance of said transducer interface is within 20% of a geometric mean of acoustic impedances of the tissue and said shockwave generating portion.

2. The system according to claim 1, wherein said transducer interface has acoustic impedance not lower than that of the tissue and not higher than that of said shockwave generating portion.

3. The system according to claim 1, wherein the acoustic impedance of said transducer interface is greater than 3.5 and said solid transducer interface comprises aluminum or copper.

4. The system according to claim 1, wherein said shockwave generating portion comprises a membrane made of an electrically conducting material.

5. The system according to claim 1, wherein said shockwave generating portion comprises a membrane comprising an electrically conducting coil.

6. The system according to claim 1, wherein a thickness of said transducer interface does not exceed 10 mm.

7. A system attachable to a surface of a tissue of a patient for applying pressure pulses to the tissue, the system comprising:
    a shockwave transducer comprising a shockwave generating portion and a solid transducer interface arranged to directly contact a tissue of a patient, said shockwave generating portion comprising an electrical-to-shockwave energy converter operable to generate pulses of pressure waves, and said transducer interface comprising an electrically safe and bio-compatible material arranged to transmit said shockwaves from said shockwave generating portion to the tissue;
    a magnet operable to induce a magnetic field in said shockwave generating portion; and
    a pulser operable to deliver electrical current pulses to said shockwave generating portion, wherein said shockwave generating portion generates shockwaves in response to said magnetic field and said electric current pulses, and wherein said magnet is operable to induce said magnetic field parallel to an outer surface of said shockwave generating portion.

8. The system according to claim 1, wherein said electrical current pulses are oriented parallel to an outer surface of said shockwave generating portion and not parallel to said magnetic field.

9. The system according to claim 1, wherein said shockwave generating portion is at least partially concave, planar or convex.

10. The system according to claim 1, wherein said pulser is operable to deliver said electrical current pulses by induction.

11. The system according to claim 1, further comprising at least one additional energy transducer operable to deliver additional energy which is at least one of optical, ultrasound, RF, magnetic, microwave and mechanical energy, and wherein delivery of the additional energy is synchronized with said electric current pulses delivered by said pulser.

12. The system according to claim 1, comprising an array of shockwave transducers of claim 1, wherein said pulser is operable to deliver the electric current pulses to said shockwave transducers in controlled trigger times so that the pressure waves simultaneously arrive at a common focal region, wherein:

$T_z$=the simultaneous arrival time of the respective waves at the focal region, $T_i$=the time of the energizing pulse associated with the $i^{th}$ transducer, $D_i$=the distance between the $i^{th}$ transducer and the focal region, and $C_i$=the average propagation speed of the wave associated with the $i^{th}$ transducer, and $T_i$ is given by: $T_i = T_z - D_i/C_i$.

13. A method for applying pressure pulses to the tissue, the method comprising:

attaching a shockwave transducer as in 1 to the tissue of a patient; and using said shockwave generating portion to generate shockwaves through said transducer interface to the tissue.

* * * * *